United States Patent
Garcia Molina et al.

(10) Patent No.: US 10,130,788 B2
(45) Date of Patent: Nov. 20, 2018

(54) SYSTEM AND METHOD FOR DETERMINING TIMING OF SENSORY STIMULATION DELIVERED TO A SUBJECT DURING A SLEEP SESSION

(71) Applicants: KONINKLIJKE PHILIPS N.V., Eindhoven (NL); Wisconsin Alumni Research Association, Madison, WI (US)

(72) Inventors: Gary Nelson Garcia Molina, Madison, WI (US); Michele Bellesi, Madison, WI (US); Brady Alexander Riedner, Middleton, WI (US); Giulio Tononi, Verona, WI (US); Juan Benzo, Madison, WI (US)

(73) Assignees: Koninklijke Philips N.V., Eindhoven (NL); Wisconsin Alumni Research Foundation, Madison, WI (US)

( * ) Notice: Subject to any disclaimer, the term of this patent is extended or adjusted under 35 U.S.C. 154(b) by 124 days.

(21) Appl. No.: 15/113,104

(22) PCT Filed: Jan. 5, 2015

(86) PCT No.: PCT/IB2015/050065
§ 371 (c)(1),
(2) Date: Jul. 21, 2016

(87) PCT Pub. No.: WO2015/118415
PCT Pub. Date: Aug. 13, 2015

(65) Prior Publication Data
US 2017/0000970 A1     Jan. 5, 2017

Related U.S. Application Data

(60) Provisional application No. 61/935,500, filed on Feb. 4, 2014.

(51) Int. Cl.
*A61M 21/02* (2006.01)
*A61B 5/00* (2006.01)
(Continued)

(52) U.S. Cl.
CPC ........... *A61M 21/02* (2013.01); *A61B 5/0476* (2013.01); *A61B 5/4812* (2013.01);
(Continued)

(58) Field of Classification Search
CPC ... A61B 5/7221; A61B 5/7246; A61B 5/0476; A61B 5/4812; A61B 5/4815;
(Continued)

(56) References Cited

U.S. PATENT DOCUMENTS

| 8,029,431 B2 | 10/2011 | Tononi |
| 2012/0251989 A1* | 10/2012 | Wetmore ............... G09B 19/00 434/236 |
| 2013/0303837 A1* | 11/2013 | Berka .................. A61M 21/02 600/28 |

FOREIGN PATENT DOCUMENTS

| JP | 2006026122 A | 2/2006 |
| WO | 2012137213 A1 | 10/2012 |

OTHER PUBLICATIONS

Tononi et al, "Sleep Function and Synaptic Homeostasis", Sleep Medicine Reviews, vol. 10, 2006, pp. 49-62.
(Continued)

*Primary Examiner* — Christine H Matthews
*Assistant Examiner* — Joshua D Lannu

(57) ABSTRACT

The present disclosure pertains to a system configured to detect transitions in sleep state of a subject during a sleep session; provide sensory stimulation to the subject with a timing based on the detected transitions in sleep state; subsequent to the sleep session, obtain reference indications of transitions in sleep state; compare the detected transitions
(Continued)

in sleep state to the reference indications of transitions in sleep state during the sleep session; based on the comparison, adjust baseline sleep state criteria to enhance correlation between detected transitions in sleep state during the sleep session using the baseline sleep state criteria and the reference indications of transitions in sleep state during the sleep session; and subsequent to adjustment of the baseline sleep state criteria, utilize the adjusted baseline sleep state criteria to detect transitions in sleep state of the subject for the purpose of controlling the one or more sensory stimulators.

15 Claims, 10 Drawing Sheets

(51) Int. Cl.
*A61B 5/0476* (2006.01)
*A61M 21/00* (2006.01)

(52) U.S. Cl.
CPC .......... *A61B 5/4815* (2013.01); *A61B 5/4836* (2013.01); *A61B 5/6803* (2013.01); *A61B 5/7221* (2013.01); *A61B 5/7225* (2013.01); *A61B 5/7246* (2013.01); *A61M 2021/0005* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2230/06* (2013.01)

(58) Field of Classification Search
CPC ... A61B 5/4836; A61B 5/6803; A61B 5/7225; A61M 2021/0005; A61M 21/02; A61M 2021/0016; A61M 2021/0022; A61M 2021/0027; A61M 2021/0044; A61M 2021/0055; A61M 2230/06
See application file for complete search history.

(56) References Cited

OTHER PUBLICATIONS

Massimini et al, "Triggering Sleep Slow Waves by Transcranial Magnetic Stimulation", Proc. Natl. Acad. Sci. vol. 104, No. 20, 2007, pp. 8496-8501.
Colrain, "The K-Complex: A 7-Decade History.," Sleep, vol. 28, No. 2, 2005, pp. 255-273.
Riedner et al, "Enhancing Sleep Slow Waves With Natural Stimuli," Medicamundi, vol. 45, No. 2, 2010, pp. 82-88.
Massimini et al, "The Sleep Slow Oscillation as a Traviling Wave", The Journal of Neuroscience, vol. 24, No. 31, 2004, pp. 6862-6870.
Tobler, "Phylogeny of Sleep Regulation," In in Principles and Practice of Sleep Medicine, 2010, pp. 77-90.

* cited by examiner

SYSTEM AND METHOD FOR DETERMINING TIMING OF SENSORY STIMULATION DELIVERED TO A SUBJECT DURING A SLEEP SESSION

CROSS-REFERENCE TO PRIOR APPLICATIONS

This application is the U.S. National Phase application under 35 U.S.C. § 371 of International Application Serial No. PCT/IB2015/050065, filed on Jan. 5, 2015, which claims the benefit of U.S. Application Ser. No. 61/935,500, filed on Feb. 4, 2014. These applications are hereby incorporated by reference herein.

BACKGROUND

1. Field

The present disclosure pertains to a system and method for determining timing of sensory stimulation delivered to a subject during a sleep session. The system utilizes information from prior sleep sessions to make predictions and/or adjustments to sleep duration parameters (e.g., baseline sleep state criteria).

2. Description of the Related Art

Systems for monitoring sleep are known. Determining sleep stages during sleep is known. Sensory stimulation during sleep is known. However, sensory stimulation during sleep is often applied continuously and/or at intervals that do not correspond to sleeping patterns of a subject. The present disclosure overcomes deficiencies in prior art systems.

SUMMARY

Accordingly, one or more aspects of the present disclosure relate to a system configured to determine timing of sensory stimulation delivered to a subject during a sleep session. The sensory stimulation is configured to increase slow wave activity and/or minimize arousals in the subject during the sleep session. The system comprises one or more sensory stimulators, one or more sensors, one or more physical computer processors, and/or other components. The one or more sensory stimulators are configured to provide sensory stimuli to the subject. The one or more sensors are configured to generate output signals conveying information related to brain activity of the subject. The one or more physical computer processors are configured by computer-readable instructions to detect transitions in sleep state of the subject during the sleep session based on the output signals and baseline sleep state criteria; control the one or more sensory stimulators to provide sensory stimulation to the subject with a timing based on the detected transitions in sleep state; subsequent to the sleep session, obtain reference indications of transitions in sleep state, the reference indications of transitions in sleep state being generated based on analysis of the output signals generated during the sleep session; compare the detected transitions in sleep state to the reference indications of transitions in sleep state; based on the comparison, adjust the baseline sleep state criteria to enhance correlation between detected transitions in sleep state during the sleep session using the baseline sleep state criteria and the reference indications of transitions in sleep state during the sleep session; and subsequent to adjustment of the baseline sleep state criteria, utilize the adjusted baseline sleep state criteria to detect transitions in sleep state of the subject for the purpose of controlling the one or more sensory stimulators.

Another aspect of the present disclosure relates to a method for determining timing of sensory stimulation delivered to a subject during a sleep session with a determination system. The sensory stimulation is configured to increase slow wave activity and/or minimize arousals in the subject during the sleep session. The system comprises one or more sensory stimulators, one or more sensors, one or more physical computer processors, and/or other components. The method comprises providing sensory stimuli to the subject with the one or more sensory stimulators; generating, with the one or more sensors, output signals conveying information related to brain activity of the subject; detecting, with the one or more physical computer processors, transitions in sleep state of the subject during the sleep session based on the output signals and baseline sleep state criteria; controlling, with the one or more physical computer processors, the one or more sensory stimulators to provide sensory stimulation to the subject with a timing based on the detected transitions in sleep state; subsequent to the sleep session, obtaining, with the one or more physical computer processors, reference indications of transitions in sleep state, the reference indications of transitions in sleep state being generated based on analysis of the output signals generated during the sleep session; comparing, with the one or more physical computer processors, the detected transitions in sleep state to the reference indications of transitions in sleep state; based on the comparison, adjusting, with the one or more physical computer processors, the baseline sleep state criteria to enhance correlation between detected transitions in sleep state during the sleep session using the baseline sleep state criteria and the reference indications of transitions in sleep state during the sleep session; and subsequent to adjustment of the baseline sleep state criteria, utilizing the adjusted baseline sleep state criteria to detect, with the one or more physical computer processors, transitions in sleep state of the subject for the purpose of controlling the one or more sensory stimulators.

Still another aspect of the present disclosure relates to a system configured to determine timing of sensory stimulation delivered to a subject during a sleep session. The sensory stimulation is configured to increase slow wave activity and/or minimize arousals in the subject during the sleep session. The system comprises means for providing sensory stimuli to the subject; means for generating output signals conveying information related to brain activity of the subject; means for detecting transitions in sleep state of the subject during the sleep session based on the output signals and baseline sleep state criteria; means for controlling the means for providing sensory stimuli to provide sensory stimulation to the subject with a timing based on the detected transitions in sleep state; subsequent to the sleep session, means for obtaining reference indications of transitions in sleep state, the reference indications of transitions in sleep state being generated based on analysis of the output signals generated during the sleep session; means for comparing the detected transitions in sleep state to the reference indications of transitions in sleep state; based on the comparison, means for adjusting the baseline sleep state criteria to enhance correlation between detected transitions in sleep state during the sleep session using the baseline sleep state criteria and the reference indications of transitions in sleep state during the sleep session; and subsequent to adjustment of the baseline sleep state criteria, means for utilizing the adjusted baseline sleep state criteria to detect transitions in sleep state of the subject for the purpose of controlling the one or more sensory stimulators.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
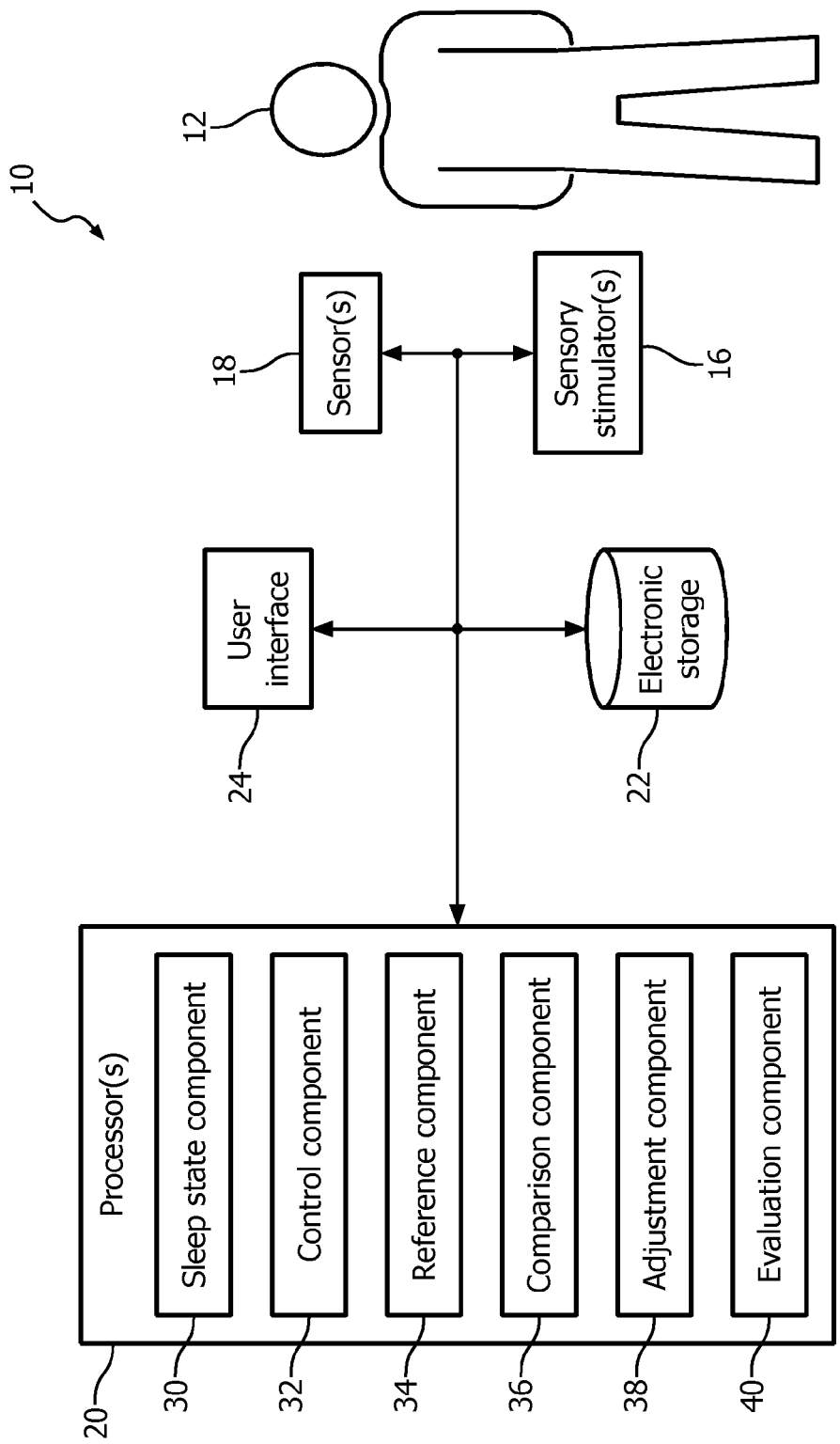
FIG. 1 is a schematic illustration of a system configured to determine timing of sensory stimulation delivered to a subject during a sleep session.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 configured to determine timing of sensory stimulation delivered to a subject 12 during a sleep session. In some embodiments, system 10 comprises one or more of a sensory stimulator 16, a sensor 18, a processor 20, electronic storage 22, a user interface 24, and/or other components. System 10 is configured to increase slow wave activity (SWA) and/or minimize arousals in subject 12 during sleep. System 10 is configured to increase SWA and/or minimize arousals in subject 12 by detecting sleep state transitions in subject 12 and then timing sensory stimulation so it is delivered during periods of deep sleep. System 10 is configured to adjust criteria used to detect sleep state transitions after individual sleep sessions so that sleep state transitions may me more accurately determined during the next sleep session. System 10 is configured to deliver the sensory stimulation during the next sleep session with a timing based on the more accurately detected sleep state transitions.

Figure 2:
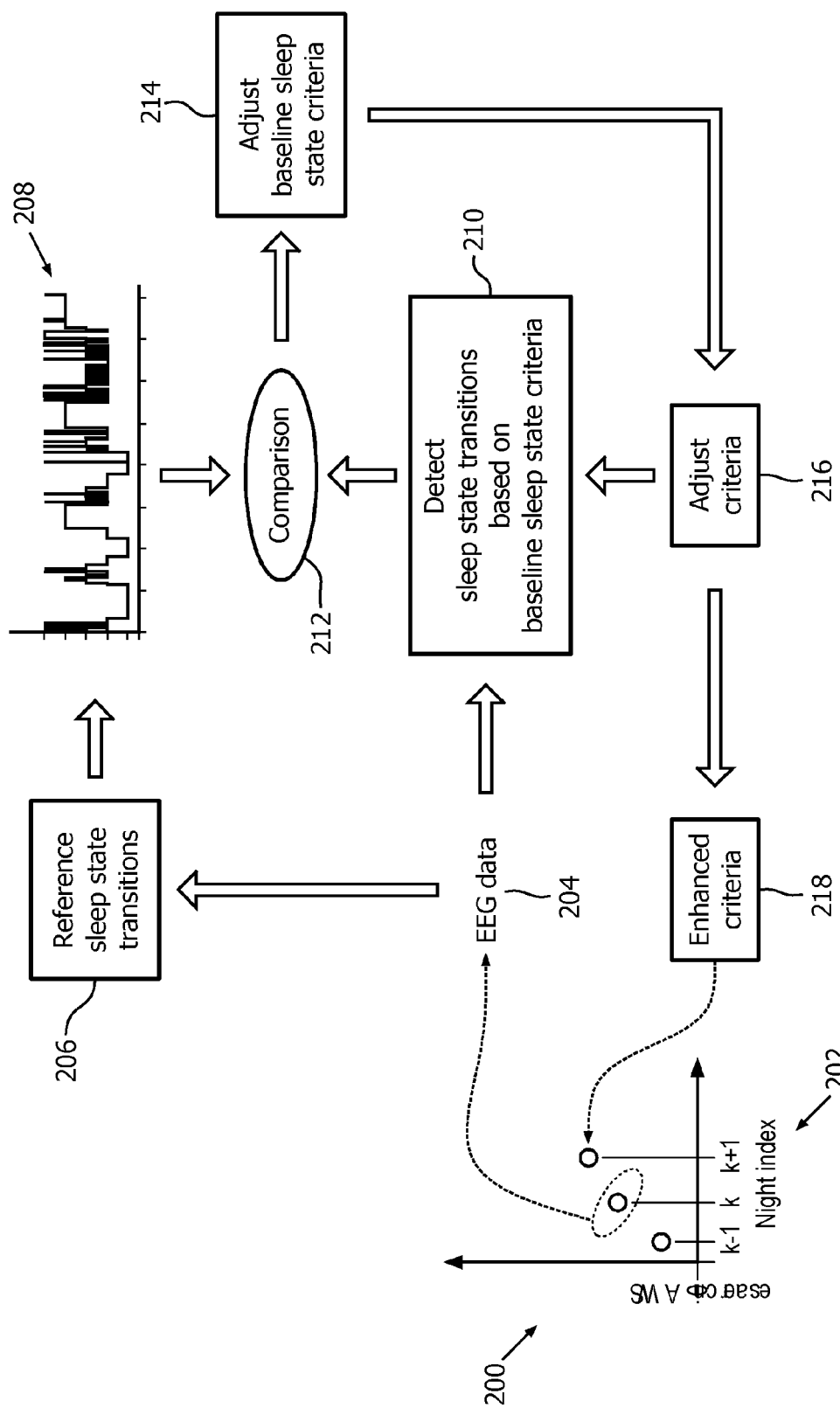
FIG. 2 summarizes the operations performed by the system to increase slow wave activity and/or minimize arousals in the subject.

FIG. 2 summarizes the operations performed by system 10 to increase SWA 200 and/or minimize arousals in subject 12. In this example, SWA increases over three nights of sleep 202. Slow wave sleep and/or SWA may be observed and/or estimated by way of an electroencephalogram (EEG). In some embodiments, SWA corresponds to the power of the EEG signal in the 0.5-4.0 Hz band. In some embodiments, this band is set to 0.5-4.5 Hz. SWA has a typical behavior throughout cyclic variations of a given sleep session. SWA increases during NREM sleep, declines before the onset of REM sleep, and remains low during REM sleep.

As shown in FIG. 2, sensor data (e.g., EEG data 204) from a previous night of sleep (e.g., a first sleep session) is used to determine reference sleep state transitions 206. The reference sleep state transitions are illustrated in automatically and/or manually scored hypnogram 208. EEG data 204 is also used 210, along with baseline sleep state criteria, to detect sleep state transitions that occurred during the previous night's sleep. The previous night's sleep state transitions were used to determine timing of sensory stimulation delivered to the subject during the previous night's sleep. The detected sleep state transitions are then compared 212 to the reference sleep state transitions. The baseline sleep state criteria are adjusted 214 based on the differences between the detected sleep state transitions and the reference sleep state transitions. The adjusted criteria 216 may continue to be iteratively adjusted one or more times until an enhanced set of criteria 218 is determined. Enhanced criteria 218 may be used to determine sleep state transitions and time the sensory stimulation during the next night of sleep (e.g., a second sleep session).

Figure 3:
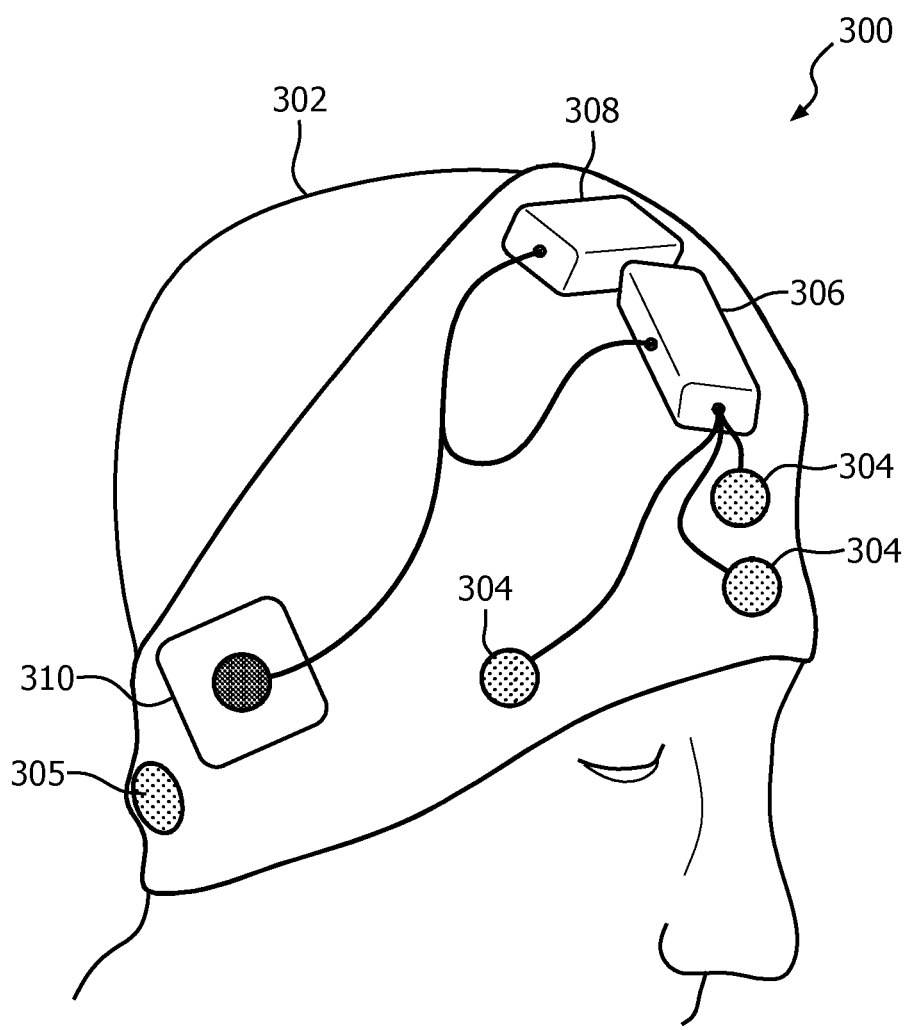
FIG. 3 illustrates a headband worn by a subject.

In FIG. 1, sensory stimulator 16, sensor 18, processor 20, electronic storage 22, and user interface 24 are shown as separate entities. This is not intended to be limiting. Some and/or all of the components of system 10 and/or other components may be grouped into one or more singular devices. For example, FIG. 3 illustrates a headband 300 worn by a subject 302. Headband 300 includes sensing electrodes 304, a reference electrode 305, one or more devices associated with an EEG 306, a wireless audio device 308, and one or more audio speakers 310. Audio speakers 310 may be located in and/or near the ears of subject 302 and/or in other locations. The reference electrode 305 may be located behind the ear of subject 302, and/or in other locations. In the example shown in FIG. 3, sensing electrodes 304 may be configured to generate output signals conveying information related to brain activity of subject 302, and/or other information. The output signals may be transmitted to a computing device (e.g., a bedside laptop) wirelessly and/or via wires. Acoustic stimulation may be delivered to subject 302 via wireless audio device 308 and/or speakers 310. Sensing electrodes 304, reference electrode 305, and devices 306 may be represented, for example, by sensor 18 in FIG. 1. Wireless audio device 308 and speakers 310 may be represented, for example, by sensory stimulator 16 shown in FIG. 1. In this example, the computing device (not shown in FIG. 3) may include processor 20, electronic storage 22, user interface 24, and/or other components of system 10 shown in FIG. 1.

Returning to FIG. 1, sensory stimulator 16 is configured to provide sensory stimuli to subject 12. Sensory stimulator 16 is configured to provide sensory stimulation to subject 12 prior to a sleep session, during a current sleep session, after a sleep session, and/or at other times. For example, sensory stimulator 16 may be configured to provide sensory stimuli to subject 12 during slow wave sleep in a sleep session. Sensory stimulator 16 may be configured to provide sensory stimulation to subject 12 during a sleep session to induce sleep slow waves and/or adjust SWA in subject 12. In some embodiments, sensory stimulator 16 may be configured such that adjusting includes increasing, decreasing, and/or other adjustment of SWA in subject 12. The manifestation of induced sleep slow waves may be measured through SWA. The delivery of the sensory stimulation is timed to correspond to sleep states associated with SWA.

Sleep states may be, include, correspond to, and/or be indicative of sleep stages in subject 12. Sleep stages of subject 12 may include one or more of NREM stage N1, stage N2, or stage N3 sleep, REM sleep, and/or other sleep stages. In some embodiments, N1 and/or N2 corresponds to a light sleep state and N3 corresponds to a deep sleep state. In some embodiments, NREM stage N3 or stage N2 sleep may be slow wave (e.g., deep) sleep. In some embodiments, slow waves may not be present throughout the whole N3 period, for example, but it may be significantly more likely that such slow waves are present during N3. Slow waves may also be present (although to a lesser extent) during N2, for example.

In some embodiments, sensory stimulator 16 may be configured to induce sleep slow waves and/or adjust SWA through non-invasive brain stimulation and/or other methods. Sensory stimulator 16 may be configured to induce and/or adjust SWA through non-invasive brain stimulation using sensory stimuli. The sensory stimuli include odors, sounds, visual stimulation, touches, tastes, and/or other stimuli. For example, transcranial magnetic stimulation may be applied to subject 12 to trigger, increase, and/or decrease SWA. As another example, sensory stimulator 16 may be configured to induce and/or adjust SWA via auditory stimulation of subject 12. Examples of sensory stimulator 16 may include one or more of a music player, a tone generator, a collection of electrodes on the scalp of subject 12, a unit to deliver vibratory stimulation (also known as somato-sensory stimulation), a coil generating a magnetic field to directly stimulate the brain's cortex, light generators, a fragrance dispenser, and/or other devices.

Sensor 18 is configured to generate output signals conveying information related to brain activity of subject 12. The brain activity of subject 12 may correspond to sleep states and/or other characteristics of subject 12. Sleep states may include, correspond to, and/or be indicative of sleep stages. The brain activity of subject 12 may be associated with sleep states and/or sleep stages that include, correspond to, and/or be indicative of rapid eye movement (REM) sleep, non-rapid eye movement (NREM) sleep, and/or other sleep (as described above, for example). Sensor 18 may comprise one or more sensors that measure such parameters directly. For example, sensor 18 may include electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16, sensor 18), or processor 20 may represent processing functionality of a plurality of devices operating in coordination.

As shown in FIG. 1, processor 20 is configured to execute one or more computer program components. The one or more computer program components may comprise one or more of a sleep state component 30, a control component 32, a reference component 34, a comparison component 36, an adjustment component 38, an evaluation component 40, and/or other components. Processor 20 may be configured to execute components 30, 32, 34, 36, 38, 40, and/or other components by software; hardware; firmware; some combination of software, hardware, and/or firmware; and/or other mechanisms for configuring processing capabilities on processor 20.

It should be appreciated that although components 30, 32, 34, 36, 38, and 40 are illustrated in FIG. 1 as being co-located within a single processing unit, in embodiments in which processor 20 comprises multiple processing units, one or more of components 30, 32, 34, 36, 38, 40, and/or other components may be located remotely from the other components. The description of the functionality provided by the different components 30, 32, 34, 36, 38, 40, and/or other components described below is for illustrative purposes, and is not intended to be limiting, as any of components 30, 32, 34, 36, 38, and/or 40 may provide more or less functionality than is described. For example, one or more of components 30, 32, 34, 36, 38, and/or 40 may be eliminated, and some or all of its functionality may be provided by other components 30, 32, 34, 36, 38, and/or 40. As another example, processor 20 may be configured to execute one or more additional components that may perform some or all of the functionality attributed below to one of components 30, 32, 34, 36, 38, and/or 40.

Sleep state component 30 is configured to detect transitions in sleep state of subject 12 during a sleep session. Sleep state component 30 is configured to detect transitions based on the output signals from sensor 18, baseline sleep state criteria, and/or other information. The baseline sleep state criteria may be determined (described below) at manufacture, determined based on previous sleep sessions of a subject, and/or determined by other methods.

Figure 4:
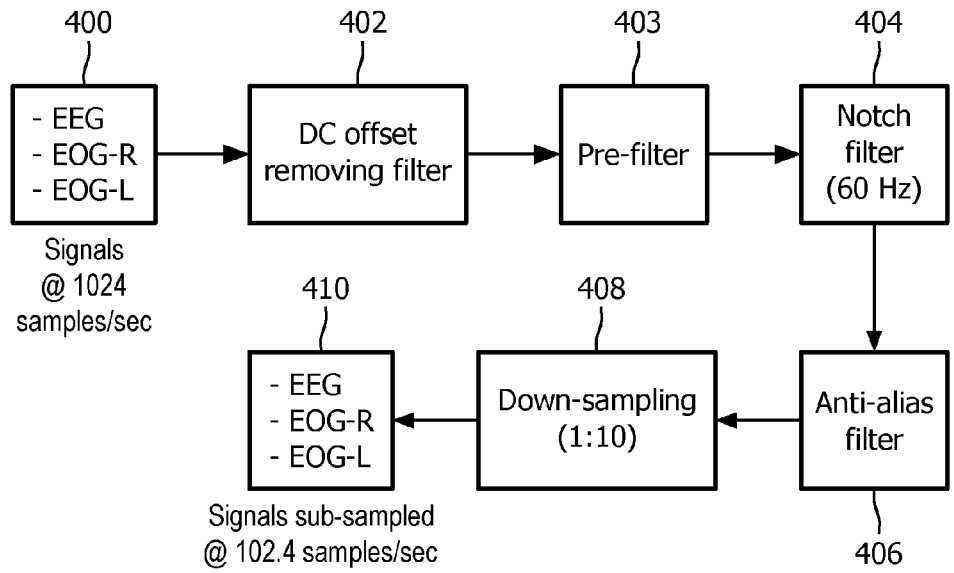
FIG. 4 illustrates multiple pre-processing steps facilitated by the sleep state component.

In some embodiments, as part of detecting transitions in sleep state, sleep state component 30 is configured to facilitate pre-processing of the output signals from sensor 18 (e.g., the EEG signal). FIG. 4 illustrates multiple pre-processing steps facilitated by sleep state component 30. The output signals from sensor 18 may include EEG signals, electrooculography right and left signals (EOG-R, EOG-L), and/or other signals 400. Pre-processing may include removing a DC offset 402, pre-filtering 403, attenuating power-line noise using a notch filter 404, for example, removing frequency components of the output signals beyond about 25 Hz using a low-pass filter, for example, using an anti-alias filter 406, down sampling 408, and/or other pre-processing operations resulting in filtered signals 410. The description of pre-processing and the illustration in FIG. 4 are not intended to be limiting. This includes any specific frequencies and/or sampling rates described herein. Pre-processing may include operations not described here, exclude some or all of the operations described above, and/or may be performed with frequencies and/or rates not described herein provided system 10 functions as described.

Figure 5:
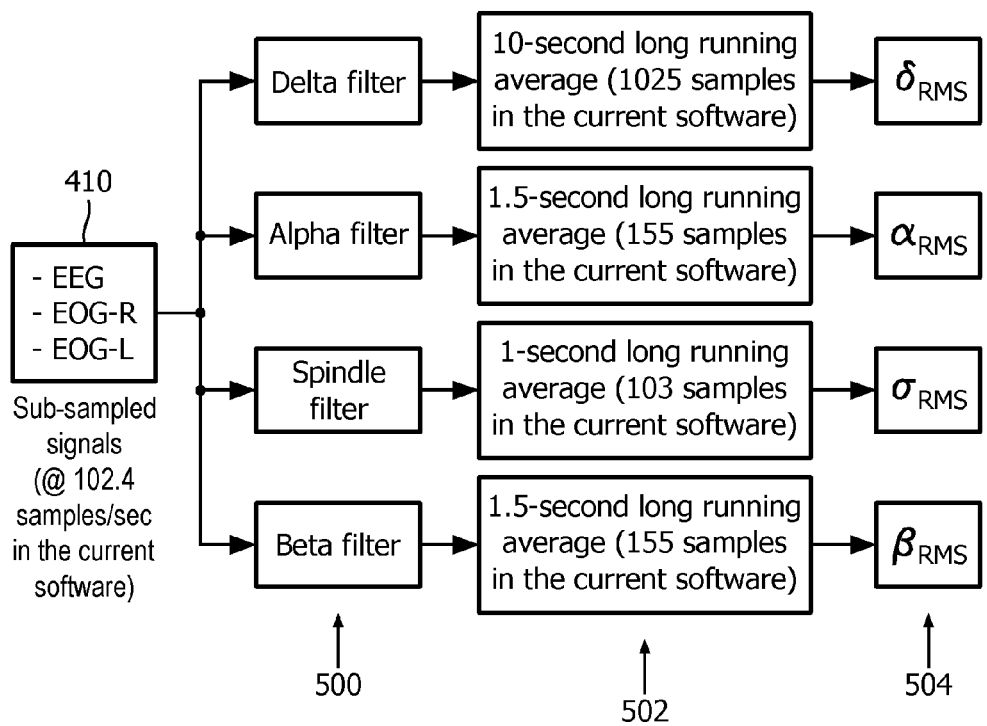
FIG. 5 illustrates EEG power estimation in RMS values for four frequency bands.

After pre-processing, sleep state component 30 (FIG. 1) may be configured to, for example, estimate EEG power, in root mean square values (RMS), for four frequency bands. FIG. 5 illustrates EEG power estimation in RMS values 504 for four frequency bands. The four frequency bands 500 are delta (0.5 to 4 Hz), alpha (8-12 Hz), sigma (11-16 Hz), and beta (15-25 Hz), for example. In some embodiments, the RMS power is estimated 502 by band-pass filtering the signal in the band of interest, squaring the signal samples resulting from the filtering, averaging over a 10-second long running window for delta, over a 1.5 second-long running window for alpha and beta, and over a 1 second-long running window for sigma, taking the square root of the averages, and/or with other operations. The shorter window duration for alpha and beta allows sleep state component 30 (FIG. 1) to detect the presence of arousals with a higher time resolution. The presence of an arousal (and/or the likelihood thereof) causes system 10 (FIG. 1) to cease and/or lower the intensity of the stimulation (in the case where the stimulation was being provided) or to delay the stimulation onset (in the case where the stimulation was not being provided). It should be noted that the specific values described above to estimate the EEG power in RMS values are given as examples and are not intended to be limiting.

Figure 6:
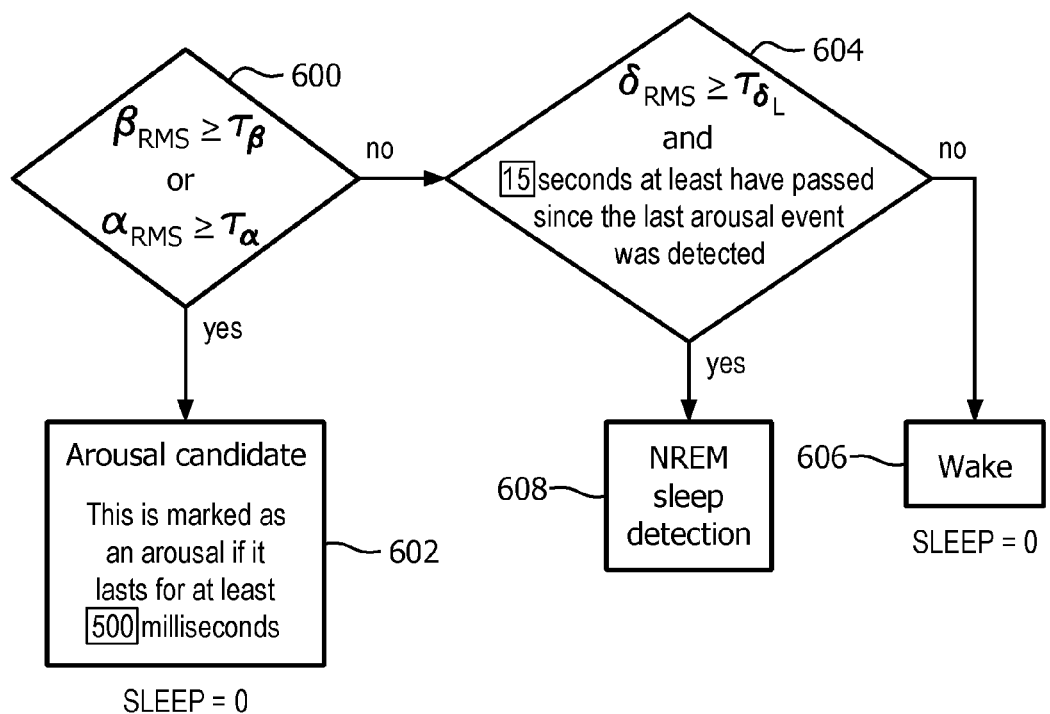
FIG. 6 illustrates example operations performed by the sleep state component to determine arousals, periods of wakefulness, and/or periods of sleep in the subject.
Figure 8:
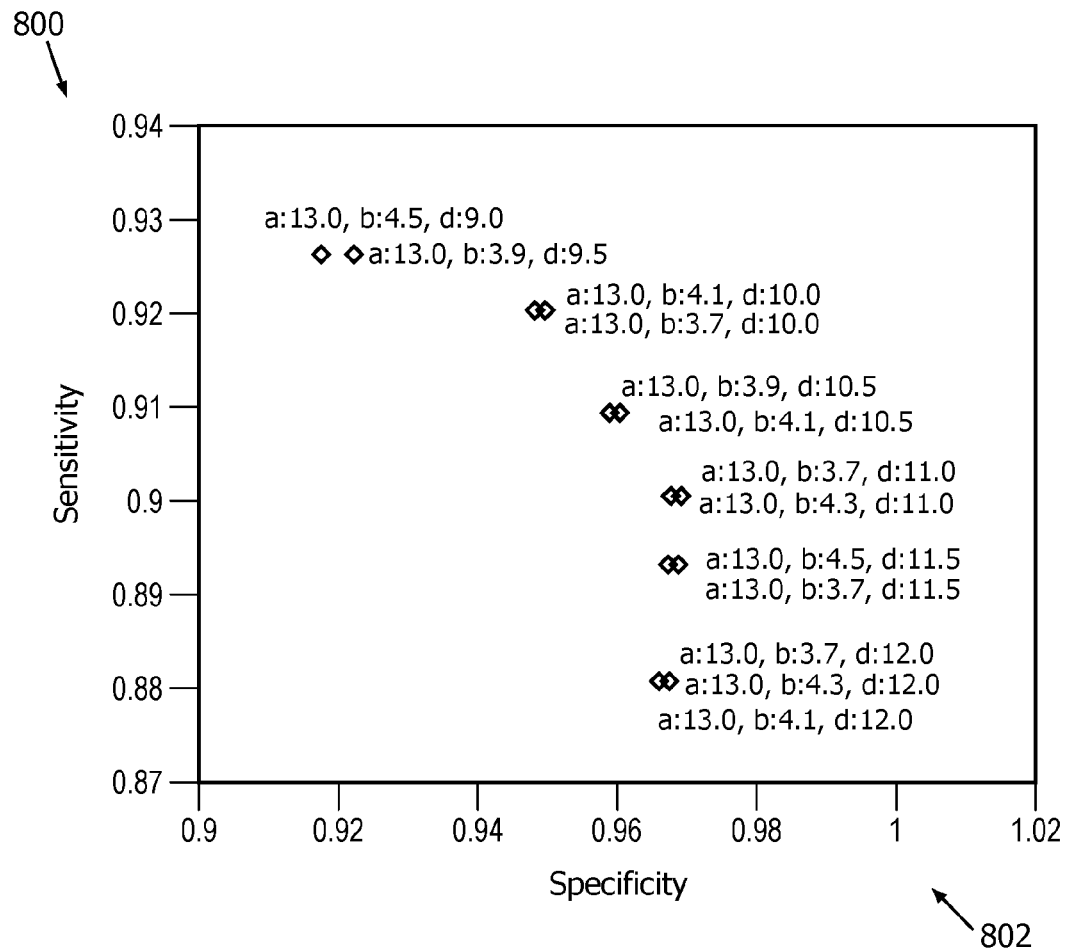
FIG. 8 illustrates sensitivity and specificity in detecting a sleep state that corresponds to and/or is sleep stage N3 as a function of values selected for individual thresholds.

FIG. 6 illustrates example operations performed by sleep state component 30 to determine arousals, periods of wakefulness, and/or periods of sleep in subject 12. The illustration in FIG. 6 and the corresponding description below should be considered non-limiting examples of further operations performed by sleep state component 30 (FIG. 1) to determine sleep states of subject 12. The RMS values in the alpha and beta bands (described above relative to FIG. 5) are used to detect the presence (and/or likelihood thereof) of an arousal. Subject 12 (FIG. 1) specific thresholds for the alpha and beta RMS values ($\tau_\alpha$ and $\tau_\beta$ and respectively) are compared 600 to the current alpha and beta RMS values (determined as described above) to detect possible arousals. These thresholds are obtained from the iterative procedure shown in FIG. 2. They are referred to as alpha threshold $\tau_\alpha$ and beta threshold $T_\beta$. They are also shown in FIG. 8 (a and b for alpha and beta threshold respectively). If the alpha or beta RMS values remain at a higher value than the respective threshold for at least 500 milliseconds, for example, then an arousal may be detected 602. If acoustic stimulation, for example, was being delivered, the detection of an arousal by sleep state component 30 (FIG. 1) causes control component 32 (FIG. 1) to stop the stimulation to prevent waking subject 12 (FIG. 1). If no arousal is detected and the last arousal detection happened at least 15 seconds, for example, in the past, then the delta RMS ($\delta_{RMS}$) value is compared 604 against a low-delta threshold $\tau_{\delta L}$. The 500 millisecond and/or the 15 second settings may be determined at manufacture, set by a user or caregiver, set by subject 12, and/or be determined by other methods. The 500 millisecond and/or the 15 second settings are examples and should not be considered limiting. If $\delta_{RMS}$ is lower than $\tau_{\delta L}$, then a default "wake" stage is assigned 606 to the currently analyzed segment of the EEG signal. In addition, a binary variable SLEEP is set to 0. If $\delta_{RMS}$ is larger than $\tau_{\delta L}$, the currently analyzed segment of the EEG signal is considered 608 non-REM sleep (e.g., the segment is assigned to a sleep state that corresponds to and/or is sleep stage N1).

Figure 7:
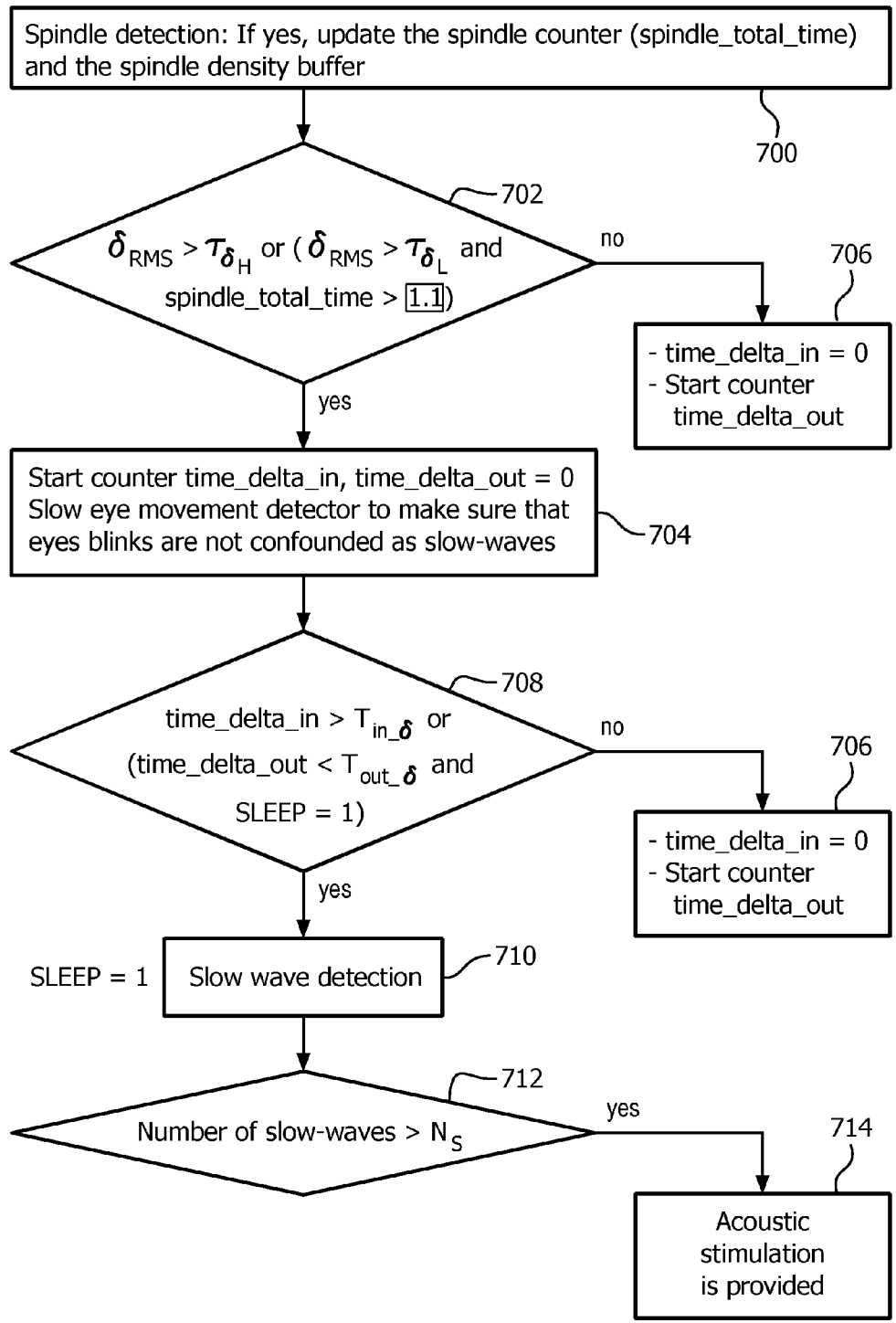
FIG. 7 illustrates operations performed by the sleep state component to detect slow wave sleep.

FIG. 7 illustrates example operations performed by sleep state component 30 to detect slow wave sleep (e.g., stage N3 sleep). FIG. 7 and the corresponding description below should not be considered limiting. Sleep state component 30 may detect slow wave sleep by any method that allows system 10 to function as described herein. Sleep state component 30 is configured to track the number of spindles detected during a sleep session and estimate a current spindle density 700. Sleep spindles may be a distinctive EEG phasic signal of NREM sleep and may be prevalent during sleep stage N2, for example. A spindle may be characterized as a group of rhythmic waves (e.g., visible in the EEG) with a progressively increasing then gradually decreasing amplitude. If the current delta RMS value ($\delta_{RMS}$) is higher than a high-delta threshold ($\delta_{\delta H}$) and/or if the RMS delta value is between the high and low delta thresholds ($\tau_{\delta L}$ and $\tau_{\delta H}$ respectively) 702 while the total time in the spindle state is longer than 1.1 seconds, for example, the sleep state may be and/or correspond to sleep stage N2, for example. A counter (time_delta_in) that keeps track of the time spent in a sleet state that is and/or corresponds to sleep stage N3 may be initialized and a counter (time_delta_out) that keeps track of the time spent in N1 or N2 (but not N3) may be set to zero 704. Otherwise 706, the counter "time_delta_out" is initialized and "time_delta_in" is set to 0. To prevent misleading eye movements from being detected as slow-waves, sensor output signals that convey information about the eyes of subject 12 may be analyzed to detect eye movements. If eye movements are detected, the signal segment is assigned to the wake state 706. Otherwise sleep state component 30 proceeds to detect slow wave sleep (e.g., stage N3 sleep). If 708 the time spent in delta sleep (tracked by "time_delta_in") is longer than a pre-defined duration parameter ($T_{in\_\delta}$) and/or if the time spent outside delta sleep (tracked by "time_delta_out") is shorter than a predefined duration parameter ($T_{out\_\delta}$) but the binary variable SLEEP is still set to 1, then the transition to a sleep state that corresponds to and/or is stage N3 sleep is detected, the binary variable SLEEP is set to 1 710, and the process to detect sleep slow waves begins. Individual sleep slow waves may be detected based on the filtered delta band signal (FIG. 5), for example. Once the number of slow waves detected 712 is larger than a predefined threshold, acoustic stimulation is provided 714. A possible value for the predefined threshold on the number of slow waves may correspond to the standard (e.g., 6 slow waves in the latest 15 seconds) that is used to categorize the deepest stage of sleep.

In some embodiments, sleep state component 30 is configured such that the baseline sleep state criteria include the thresholds $\tau_\beta$, $\tau_\alpha$, $\tau_{\delta H}$, and/or other criteria. As described above, the thresholds influence the detection of slow wave sleep, arousals, and/or wake periods. The thresholds and/or other baseline sleep state criteria may be determined at manufacture, set by a user (e.g., a doctor, a caregiver, subject 12, etc.) via user interface 24, may be determined based on previous sleep sessions of subject 12, and/or be determined by other methods. By way of non-limiting example, default values for these thresholds may be $\tau_\beta$=3.5, $\tau_\alpha$=13, and $\tau_{\delta H}$=11. The default values may be determined by a user (e.g., subject 12, a doctor, a caregiver) based on previous experience with system 10, determined based on previous sleep sessions of subject 12, and/or determined by other methods. In some embodiments, the default values for the thresholds may be obtained from a user via entry and/or selection through user interface 24. Increasing (and/or decreasing) the beta threshold (t) makes sleep state component 30 (FIG. 1) less (and/or more) sensitive to arousals and increasing (and/or decreasing) the delta threshold ($\tau_{\delta H}$) makes the sleep state component 30 (FIG. 1) less (and/or more) sensitive to the detection of deep sleep.

Returning to FIG. 1, control component 32 is configured to control sensory stimulator 16 to provide sensory stimulation to subject 12. Control component 32 is configured to control sensory stimulator 16 to provide sensory stimulation to subject 12 with a timing based on transitions in sleep state detected by sleep state component 30, and/or other information. In some embodiments, control component 32 is configured such that the timing of the sensory stimulation corresponds to slow wave (e.g., stage N2 and/or stage N3) sleep, and/or other sleep states (determined as described above related to FIG. 4-FIG. 7).

Reference component 34 is configured to obtain reference indications of transitions in sleep state. Reference component 34 is configured to obtain reference indications of transitions in sleep state subsequent to a sleep session. Reference component 34 is configured such that the reference indications of transitions in sleep state are generated based on analysis of the output signals from sensor 18 generated during the preceding sleep session, and/or other information. The analysis of the output signals from sensors 18 may include manual and/or automated generation of a reference hypnogram, and/or other analysis. The reference sleep state transitions are determined in an offline manner. This offline process may be A) manual, where the reference hypnogram is determined by a sleep expert after visual examination and scoring of the recorded data, and/or B) automated where an existing algorithm determines the sleep staging. This automated process is more accurate than an online method (and may be used as a reference) because the offline algorithm can have access to the signal in a non-causal manner (e.g., the algorithm has access to the future which can enable the smoothing of the results).

Comparison component 36 is configured to compare the detected transitions in sleep state to the reference indications of transitions in sleep state. The comparison may be made after a sleep session is complete and/or at other times. The comparison may be made using the information conveyed by sensor 18, information determined by sleep state component 30, information obtained by reference component 34, information received via user interface 24, information stored in electronic storage 22, and/or other information. In some embodiments, comparing the detected transitions in sleep state to the reference indications of transitions in sleep state during the sleep session may include comparing detected sleep states and/or stages to reference sleep states and/or stages one or more times during the sleep session. For example, comparison component 36 may be configured to generate a hypnogram for the sleep session using the detected sleep state transitions. Comparison component 36 may compare the detection based hypnogram to the reference hypnogram obtained by reference component 34 at one or more time points during the sleep session. Comparison component 36 may determine whether the sleep stage of the detection based hypnogram matches the sleep stage of the reference hypnogram at the one or more time points during the sleep session.

In some embodiments, comparing the detected transitions in sleep state to the reference indications of transitions in sleep state during the sleep session may include providing an indication of a level of agreement between the detected transitions and the reference indications of transitions. Continuing with the example above, comparison component 36 may indicate a higher level of agreement between hypnograms when transitions between sleep stages in the detection based hypnogram occur at the same time as transitions between the same two sleep stages in the reference hypnogram during the sleep session.

Adjustment component 38 is configured to adjust the baseline sleep state criteria. Adjustment component 38 is configured to adjust the baseline sleep state criteria to enhance correlation between detection of transitions in sleep state (e.g., by sleep state component 30) during the sleep session using the baseline sleep state criteria and the reference indications of transitions in sleep state during the sleep session (e.g., obtained by reference component 34). Adjustment component 38 is configured to adjust the baseline sleep stage criteria based on the comparison by comparison component 36, and/or other information. Subsequent to adjustment of the baseline sleep state criteria, sleep state component 30 is configured to utilize the adjusted baseline sleep state criteria to detect transitions in sleep state of the subject for the purpose of controlling the one or more sensory stimulators.

In some embodiments, adjustment of the baseline sleep state criteria is based on a user's prior experience with system 10, prior sleep sessions of subject 12, and/or other information. Based on prior knowledge of system 10, a user may determine and/or select (e.g., via user interface 24) sets of possible values for individual sleep state criteria. By way of a non-limiting example, for thresholds $\tau_\beta$, $\tau_\alpha$, and $\tau_{\delta H}$, values may include:

$\tau_\beta = 3.5 + k\Delta\beta, \Delta\beta = 0.1; k = 5, \ldots, 5$ $\tau_\alpha = 12 + k\Delta\alpha, \Delta\alpha = 1; k = -2, \ldots, 2$ $\tau_{\delta H} = 11 + k\Delta\delta, \Delta\delta = 1; k = -2, \ldots, 2$ All possible triplet combinations of the values for thresholds $\tau_\beta$, $\tau_\alpha$, $\tau_{\delta H}$ may be tested by adjustment component 38 using the EEG data from the previous sleep session. An enhanced set of values for the thresholds may be determined by considering the resulting sensitivity to changes in sleep state and the resulting specificity in detecting a specific sleep state relative to other sleep states (e.g., detecting that a current sleep state corresponds to and/or is N3, and not N2) and/or arousals.

FIG. 8 illustrates sensitivity 800 and specificity 802 in detecting a sleep state that corresponds to and/or is sleep stage N3 as a function of values selected for individual thresholds. In FIG. 8, "b", "a", and "d", refer to $\tau_\beta$, $\tau_\alpha$, and $\tau_{\delta H}$ respectively. For example, under a first (e.g., "no-harm") strategy, system 10 (FIG. 1) is configured to deliver stimulation without disturbing the sleep of subject 12 (FIG. 1). In this case, the goal is to achieve a high specificity in detecting N3 and a high sensitivity in detecting arousals. Alternatively, the strategy may be to maximize the effect of the sensory stimulation in which case a higher sensitivity in detecting N3 is sought while keeping a reasonably high sensitivity in detecting arousals.

Returning to FIG. 1, in some embodiments, adjustment of the baseline sleep state criteria is based on an empirical estimation of a gradient of the cumulative slow wave activity. This approach may be expressed in terms of the following equation:

$$\begin{pmatrix} \tau_\alpha(n) \\ \tau_\beta(n) \\ \tau_{\delta H}(n) \end{pmatrix} = \begin{pmatrix} \tau_\alpha(n-1) \\ \tau_\beta(n-1) \\ \tau_{\delta H}(n-1) \end{pmatrix} + \mu_n \begin{pmatrix} \frac{\partial SWA}{\partial \tau_\alpha} \\ \frac{\partial SWA}{\partial \tau_\beta} \\ \frac{\partial SWA}{\partial \tau_{\delta H}} \end{pmatrix}$$

In this equation, "n" represents the iteration index, "∂" stands for the partial derivative, and "$\mu_n$" is an updating factor. The updating factor is usually a small positive number (e.g., because the goal is to maximize the SWA) which may vary between iterations. A positive value for the updating factor indicates that adjustment component 38 is adjusting the baseline sleep state criteria to detect sleep states so sensory stimulation may be timed to achieve an increase in SWA.

Figure 9:
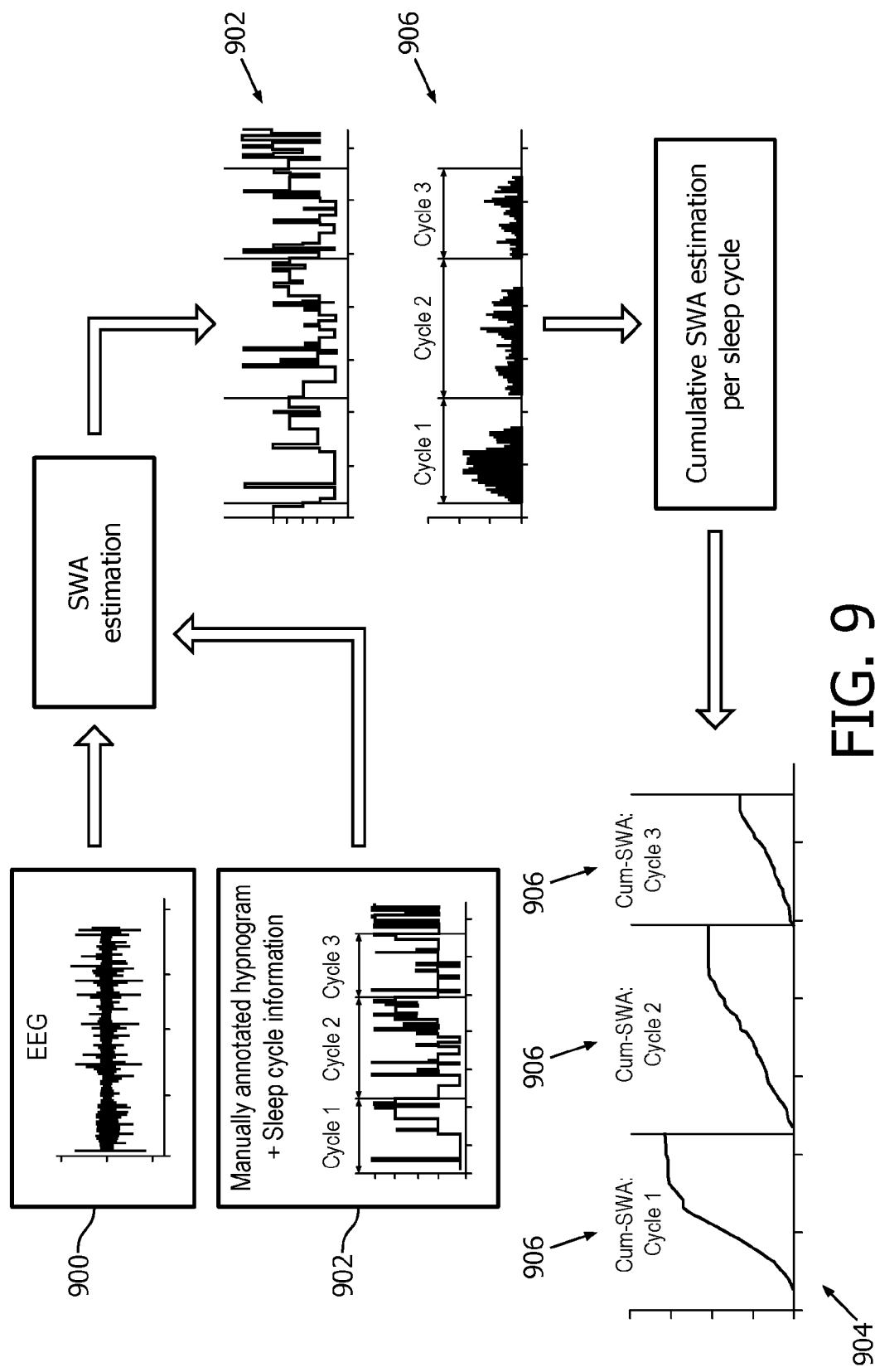
FIG. 9 illustrates determining cumulative slow wave activity.

FIG. 9 illustrates determining cumulative slow wave activity. EEG power in the delta (0.5 to 4 Hz) band (e.g., SWA) 900 is estimated for individual epochs of time during a sleep session that that correspond to and/or are sleep stage N2 and/or N3 sleep. Typical epoch duration may be about 30 seconds, for example. The summation 904 of this power over a pre-specified number of sleep cycles 906 is termed the cumulative SWA. A sleep cycle corresponds to an orderly progression through succession of sleep stages from light sleep to deep sleep and followed by rapid eye movement (REM) sleep. In some embodiments, SWA is not accumulated for N1, Wake and/or REM epochs. The estimation of the cumulative SWA is based on a hypnogram 902 of the sleep session. The hypnogram may be manually determined, may be determined in an automated way, and/or may be determined by other methods.

Returning to FIG. 1, evaluation component 40 is configured to determine a performance metric that indicates whether the adjustment of the baseline sleep state criteria was effective. In some embodiments, the performance metric is cumulative slow wave activity. As described above relative to FIG. 9, cumulative slow wave activity is a summation of EEG power in the delta band for individual N2 and/or N3 sleep stage epochs for a pre-determined number of sleep cycles. The higher the cumulative SWA, the more effective adjustment to the baseline sleep state criteria. In some embodiments, evaluation component 40 is configured to evaluate whether the adjustment of the baseline sleep state criteria was effective based on a sleep session subsequent to the adjustment of the baseline criteria. For example, the baseline sleep state criteria may be adjusted as described above based on Tuesday night's sleep. The adjusted criteria may be used by system 10 on Wednesday night to determine sleep states and time sensory stimulation. The effectiveness of the adjusted criteria may be determined by evaluation component 40 based on Wednesday night's sleep. Evaluation component 40 may determine the cumulative slow wave activity for Wednesday night and compare it to the cumulative slow wave activity for Tuesday night to determine whether the adjustments to the baseline criteria were effective.

In some embodiments, the performance metric is related to the behavior and/or emotions of subject 12 after the sleep session, sleep disturbance in subject 12 during the sleep session, and/or other performance metrics. For example, cognitive performance indicators (e.g., memory and/or vigilance), behavior reports, mental refreshedness indicator, a subjective sleep quality indicator, and/or other indicators may be used as a performance metric. In some embodiments, the alternative performance metrics may be correlated to objectively determined parameters related to the stimulation. The alternative performance metrics may be correlated to objectively determined sensory stimulation parameters such as total number of acoustic tones delivered, average volume of the stimulation, maximum volume of the stimulation, and/or other parameters. As a result, the objectively determined parameters may be correlated with increases and/or decreases in SWA and adjusted based on the SWA.

Figure 10:
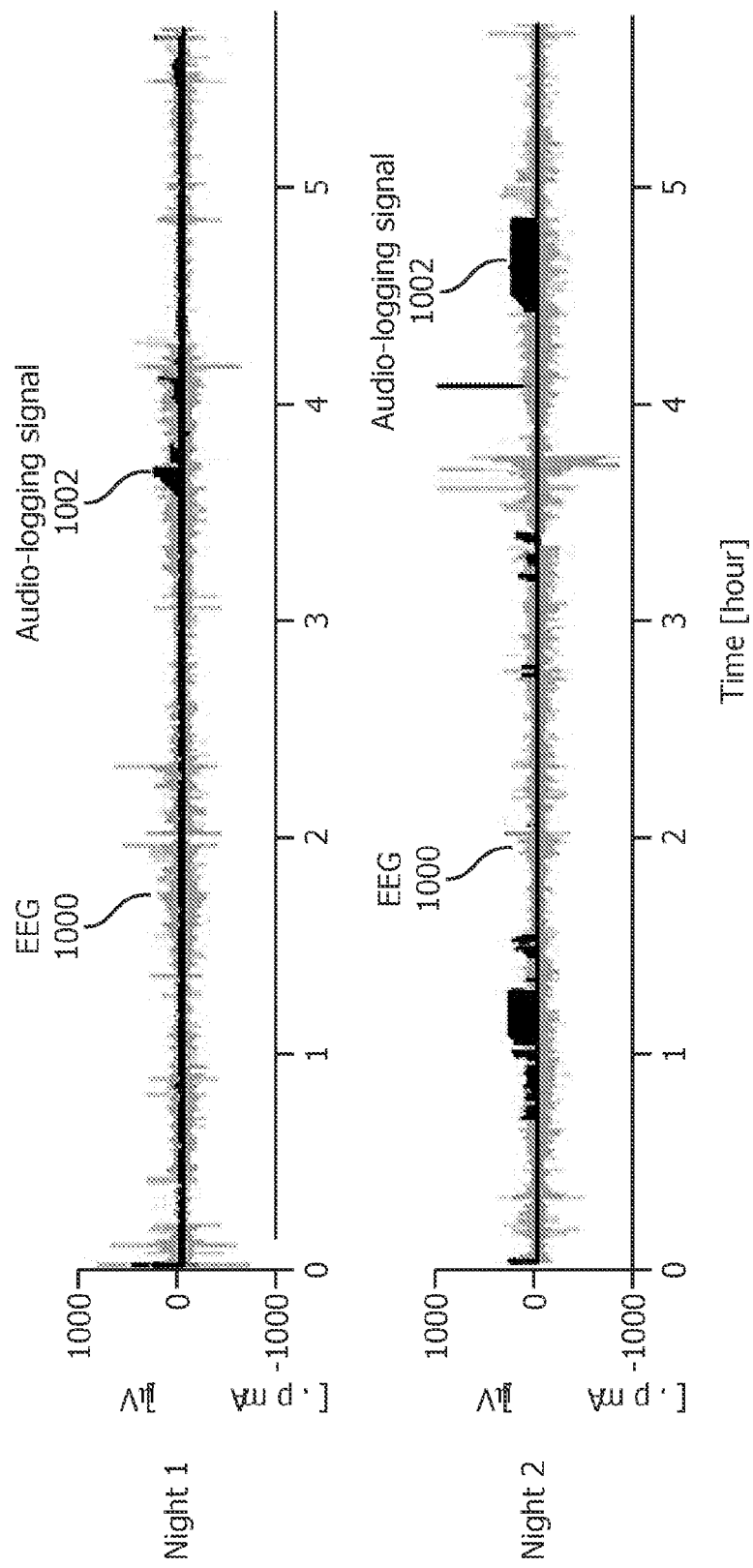
FIG. 10 illustrates an example of increased auditory sensory stimulation for a second sleep session (Night 2) compared to a first sleep session (Night 1).

FIG. 10 illustrates an example of increased auditory sensory stimulation for a second sleep session (Night 2) compared to a first sleep session (Night 1). In this example, the auditory sensory stimulation delivered on Night 1 was based on sleep state transitions determined using baseline sleep state criteria. The increased auditory stimulation for Night 2 was delivered based on sleep state transitions determined using sleep state criteria adjusted by system 10 (FIG. 1) as described above. The EEG signal 1000 and the log of the acoustic stimulation 1002 illustrate that adjusting the parameters led to more abundant stimulation during Night 2. The more abundant stimulation may be the result of, for example, control component 32 (FIG. 1) controlling sensory stimulator 16 (FIG. 1) to deliver sensory stimulation based on more precise sleep state (e.g., sleep stage) transition determinations by sleep state component 30 (FIG. 1) because sleep state component 30 was using adjusted sleep state criteria during Night 2.

More precise sleep state transition determinations may refer to a situation where, for example, because of high alpha power (e.g., determined from the EEG) during periods of deep sleep, several false arousals are detected. These false arousals prevent system 10 from delivering sensory stimulation. If system 10 operated using the parameters from this baseline night without adjustment, no stimulation would be provided during future sleep sessions. However, after adjustment of the baseline sleet state criteria, even though the high alpha power may persist during the deep sleep periods, system 10 determines that subject 12 (FIG. 1) is actually in deep sleep and continues to deliver sensory stimulation.

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms (e.g., adjustment algorithms used to adjust the baseline sleep state criteria), algorithm inputs (e.g., the baseline sleep state criteria), information determined by processor 20 (e.g., the adjusted sleep state criteria), information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10. For example, user interface 24 may display an EEG to a user. This enables data, cues, results, instructions, and/or any other communicable items, collectively referred to as "information," to be communicated between a user (e.g., subject 12, a doctor, a caregiver, and/or other users) and one or more of sensory stimulator 16, sensor 18, processor 20, electronic storage 22, and/or other components of system 10.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with processor 20, sensory stimulator 16, and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 11:
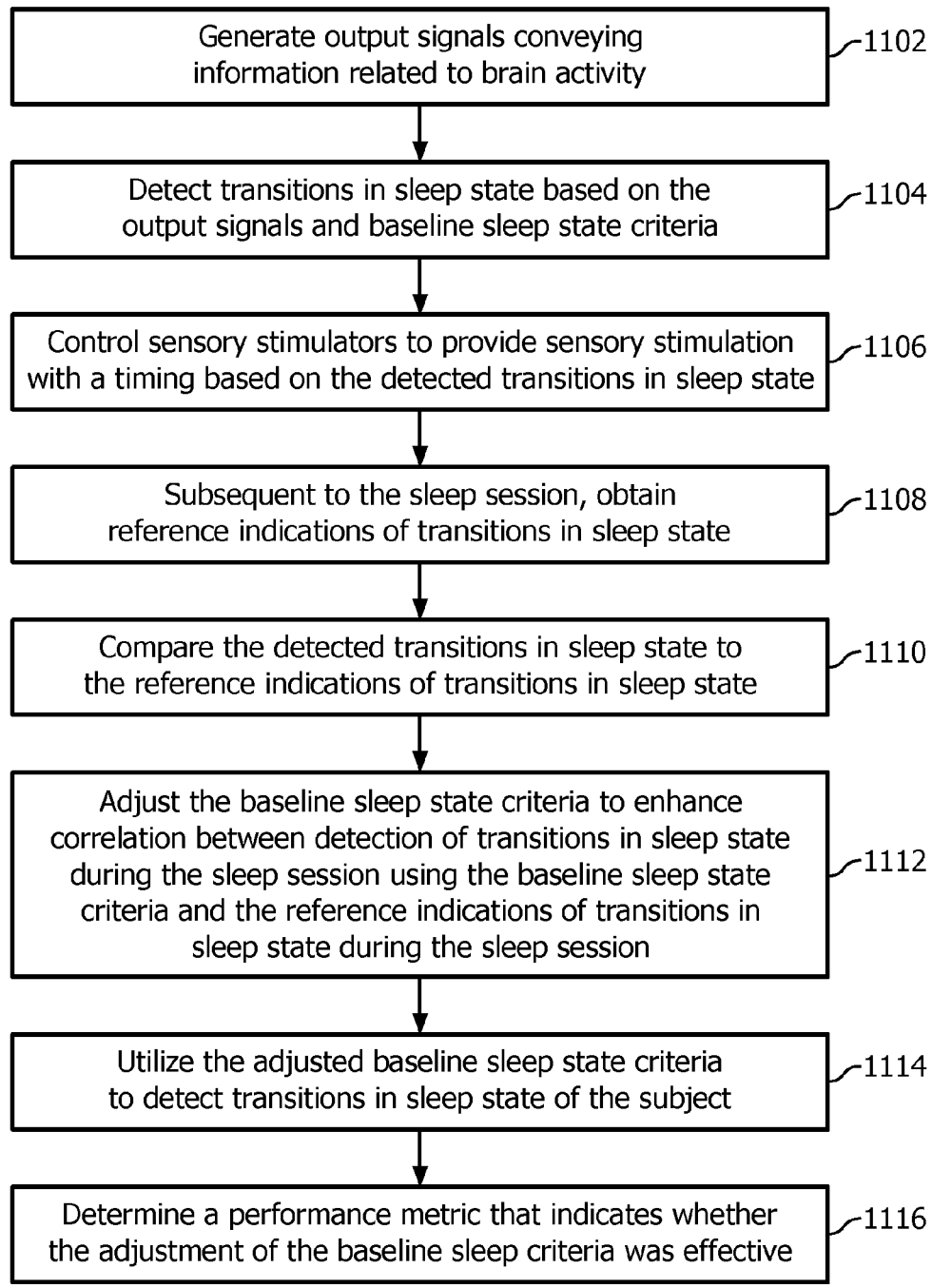
FIG. 11 illustrates a method for determining timing of sensory stimulation delivered to a subject during a sleep session with a determination system.

FIG. 11 illustrates a method 1100 for determining timing of sensory stimulation delivered to a subject during a sleep session with a determination system. The sensory stimulation is configured to increase slow wave activity, minimize arousals, and/or facilitate other behavior in the subject during the sleep session. The system comprises one or more sensory stimulators, one or more sensors, one or more physical computer processors, and/or other components. The one or more processors are configured to execute one or more computer program components. The one or more computer program components may comprise one or more of a sleep state component 30, a control component 32, a reference component 34, a comparison component 36, an adjustment component 38, an evaluation component 40, and/or other components. The operations of method 1100 presented below are intended to be illustrative. In some embodiments, method 1100 may be accomplished with one or more additional operations not described, and/or without one or more of the operations discussed. Additionally, the order in which the operations of method 1100 are illustrated in FIG. 11 and described below is not intended to be limiting.

In some embodiments, method 1100 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1100 in response to instructions stored electronically on an electronic storage medium. The one or more processing devices may include one or more devices configured through hardware, firmware, and/or software to be specifically designed for execution of one or more of the operations of method 1100.

At an operation 1102, output signals conveying information related to brain activity of the subject during a sleep session are generated. In some embodiments, operation 1102 is performed by one or more sensors the same as or similar to sensors 18 (shown in FIG. 1 and described herein).

At an operation 1104, transitions in sleep state are detected. The transitions in sleep state are detected during the sleep session based on the output signals, baseline sleep state criteria, and/or other information. In some embodiments, operation 1104 is performed by a computer processor component the same as or similar to sleep state component 30 (shown in FIG. 1 and described herein).

At an operation 1106, sensory stimulators are controlled to provide sensory stimulation to the subject with a timing based on the detected transitions in sleep state. In some embodiments, operation 1106 is performed by a computer processor component the same as or similar to control component 32 (shown in FIG. 1 and described herein).

At an operation 1108, reference indications of transitions in sleep state are obtained. The reference indications are obtained subsequent to the sleep session of the subject. The reference indications are generated based on an analysis of the output signals generated during the sleep session. In some embodiments, operation 1108 is performed by a computer processor component the same as or similar to reference component 34 (shown in FIG. 1 and described herein).

At an operation 1110, the detected transitions in sleep state are compared to the reference indications of transitions in sleep state. In some embodiments, operation 1110 is performed by a computer processor component the same as or similar to comparison component 36 (shown in FIG. 1 and described herein).

At an operation 1112, based on the comparison, the baseline sleep state criteria are adjusted to enhance correlation between detection of transitions in sleep state during the sleep session using the baseline sleep state criteria and the reference indications of transitions in sleep state during the sleep session. In some embodiments, adjustment of the baseline sleep state criteria is based on an empirical estimation of a gradient of the cumulative slow wave activity. In some embodiments, operation 1112 is performed by a computer processor component the same as or similar to adjustment component 38 (shown in FIG. 1 and described herein).

At an operation 1114, subsequent to adjustment of the baseline sleep state criteria, the adjusted baseline sleep state criteria are utilized to detect transitions in sleep state of the subject. The adjusted baseline sleep state criteria are utilized for the purpose of controlling the one or more sensory stimulators. In some embodiments, operation 1114 is performed by a computer processor component the same as or similar to sleep state component 30 (shown in FIG. 1 and described herein).

At an operation 1116, a performance metric that indicates whether the adjustment of the baseline sleep state criteria was effective is determined. In some embodiments, the performance metric is cumulative slow wave activity. Cumulative slow wave activity is a summation of EEG power in a delta band for individual N2 and/or N3 sleep stage epochs for a pre-determined number of sleep cycles. In some embodiments, the performance metric is related to the behavior and/or emotions of the subject after the sleep session, sleep disturbance in the subject during the sleep session, and/or other performance metrics. In some embodiments, operation 1116 is performed by a computer processor component the same as or similar to evaluation component 40 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to determine timing of sensory stimulation delivered to a subject during a sleep session, the sensory stimulation configured to increase slow wave activity and minimize arousals in the subject during the sleep session, the system comprising:

one or more sensory stimulators configured to provide sensory stimuli to the subject;

one or more sensors configured to generate output signals conveying information related to brain activity of the subject; and one or more physical computer processors configured by computer-readable instructions to:

detect transitions in a sleep state of the subject during the sleep session based on the output signals and baseline sleep state criteria, the baseline sleep state criteria comprising one or more thresholds for one or more corresponding parameters determined based on the information related to brain activity of the subject;

control the one or more sensory stimulators to provide the sensory stimulation to the subject with a timing based on the detected transitions in the sleep state;

subsequent to the sleep session, obtain reference indications of transitions in the sleep state, the reference indications of transitions in the sleep state being generated based on analysis of the output signals generated during the sleep session;

compare the detected transitions in the sleep state to the reference indications of transitions in the sleep state;

based on the comparison, adjust the baseline sleep state criteria to enhance correlation between the detected transitions in the sleep state during the sleep session using the baseline sleep state criteria and the reference indications of transitions in the sleep state during the sleep session; and subsequent to adjustment of the baseline sleep state criteria, utilize the adjusted baseline sleep state criteria to detect transitions in the sleep state of the subject and control the one or more sensory stimulators.

2. The system of claim 1, wherein the one or more physical computer processors are further configured to determine a performance metric related to slow wave activity in the subject that indicates whether the adjustment of the baseline sleep state criteria enhanced the correlation between the detected transitions in a sleep state during the sleep session using the baseline sleep state criteria and the reference indications of transitions in the sleep state during the sleep session.

3. The system of claim 2, wherein the one or more physical computer processors are configured such that the performance metric is cumulative slow wave activity.

4. The system of claim 3, wherein the one or more physical computer processors are configured such that adjustment of the baseline sleep state criteria is based on an empirical estimation of a gradient of the cumulative slow wave activity.

5. A system configured to determine timing of sensory stimulation delivered to a subject during a sleep session, the sensory stimulation configured to increase slow wave activity and minimize arousals in the subject during the sleep session, the system comprising:

one or more sensory stimulators configured to provide sensory stimuli to the subject;

one or more sensors configured to generate output signals conveying information related to brain activity of the subject; and one or more physical computer processors configured by computer-readable instructions to:

detect transitions in a sleep state of the subject during the sleep session based on the output signals and baseline sleep state criteria;

control the one or more sensory stimulators to provide the sensory stimulation to the subject with a timing based on the detected transitions in the sleep state;

subsequent to the sleep session, obtain reference indications of transitions in the sleep state, the reference indications of transitions in the sleep state being generated based on analysis of the output signals generated during the sleep session;

compare the detected transitions in the sleep state to the reference indications of transitions in the sleep state;

based on the comparison, adjust the baseline sleep state criteria to enhance correlation between the detected transitions in the sleep state during the sleep session using the baseline sleep state criteria and the reference indications of transitions in the sleep state during the sleep session;

subsequent to adjustment of the baseline sleep state criteria, utilize the adjusted baseline sleep state criteria to detect transitions in the sleep state of the subject and control the one or more sensory stimulators; and determine a performance metric related to slow wave activity in the subject that indicates whether the adjustment of the baseline sleep state criteria enhanced the correlation between the detected transitions in the sleep state during the sleep session using the baseline sleep state criteria and the reference indications of transitions in the sleep state during the sleep session, wherein the performance metric is cumulative slow wave activity, and wherein the cumulative slow wave activity is a summation of EEG power in a delta band for individual N2 and/or N3 sleep stage epochs for a pre-determined number of sleep cycles.

6. A method for determining timing of sensory stimulation delivered to a subject during a sleep session with a determination system, the sensory stimulation configured to increase slow wave activity and minimize arousals in the subject during the sleep session, the system comprising one or more sensory stimulators, one or more sensors, and one or more physical computer processors, the method comprising:

generating, with the one or more sensors, output signals conveying information related to brain activity of the subject;

detecting, with the one or more physical computer processors, transitions in a sleep state of the subject during the sleep session based on the output signals and baseline sleep state criteria, the baseline sleep state criteria comprising one or more thresholds for one or more corresponding parameters determined based on the information related to brain activity of the subject;

controlling, with the one or more physical computer processors, the one or more sensory stimulators to provide the sensory stimulation to the subject with a timing based on the detected transitions in the sleep state;

subsequent to the sleep session, obtaining, with the one or more physical computer processors, reference indications of transitions in the sleep state, the reference indications of transitions in the sleep state being generated based on analysis of the output signals generated during the sleep session;

comparing, with the one or more physical computer processors, the detected transitions in the sleep state to the reference indications of transitions in the sleep state;

based on the comparison, adjusting, with the one or more physical computer processors, the baseline sleep state criteria to enhance correlation between the detected transitions in the sleep state during the sleep session using the baseline sleep state criteria and the reference indications of transitions in the sleep state during the sleep session; and subsequent to adjustment of the baseline sleep state criteria, utilizing the adjusted baseline sleep state criteria to detect, with the one or more physical computer processors, transitions in the sleep state of the subject, and control the one or more sensory stimulators.

7. The method of claim 6, further comprising determining, with the one or more physical computer processors, a performance metric related to slow' wave activity in the subject that indicates whether the adjustment of the baseline sleep state criteria enhanced the correlation between the detected transitions in a sleep state during the sleep session using the baseline sleep state criteria and the reference indications of transitions in the sleep state during the sleep session.

8. The method of claim 7, wherein the performance metric is cumulative slow wave activity.

9. The method of claim 8, wherein adjustment of the baseline sleep state criteria is based on an empirical estimation of a gradient of the cumulative slow wave activity.

10. A method for determining timing of sensory stimulation delivered to a subject during a sleep session with a determination system, the sensory stimulation configured to increase slow wave activity and minimize arousals in the subject during the sleep session, the system comprising one or more sensory stimulators, one or more sensors, and one or more physical computer processors, the method comprising:

generating, with the one or more sensors, output signals conveying information related to brain activity of the subject;

detecting, with the one or more physical computer processors, transitions in a sleep state of the subject during the sleep session based on the output signals and baseline sleep state criteria;

controlling, with the one or more physical computer processors, the one or more sensory stimulators to provide the sensory stimulation to the subject with a timing based on the detected transitions in the sleep state;

subsequent to the sleep session, obtaining, with the one or more physical computer processors, reference indications of transitions in the sleep state, the reference indications of transitions in the sleep state being generated based on analysis of the output signals generated during the sleep session;

comparing, with the one or more physical computer processors, the detected transitions in the sleep state to the reference indications of transitions in the sleep state;

based on the comparison, adjusting, with the one or more physical computer processors, the baseline sleep state criteria to enhance correlation between the detected transitions in the sleep state during the sleep session using the baseline sleep state criteria and the reference indications of transitions in the sleep state during the sleep session;

subsequent to adjustment of the baseline sleep state criteria, utilizing the adjusted baseline sleep state criteria to detect, with the one or more physical computer processors, transitions in the sleep state of the subject, and control the one or more sensory stimulators; and determining, with the one or more physical computer processors, a performance metric related to slow wave activity in the subject that indicates whether the adjustment of the baseline sleep state criteria enhanced the correlation between the detected transitions in the sleep state during the sleep session using the baseline sleep state criteria and the reference indications of transitions in the sleep state during the sleep session, wherein the performance metric is cumulative slow wave activity, and wherein the cumulative slow wave activity is a summation of EEG power in a delta band for individual N2 and/or N3 sleep stage epochs for a pre-determined number of sleep cycles.

11. A system configured to determine timing of sensory stimulation delivered to a subject during a sleep session, the sensory stimulation configured to increase slow wave activity and minimize arousals in the subject during the sleep session, the system comprising:

means for providing sensory stimuli to the subject;

means for generating output signals conveying information related to brain activity of the subject;

means for detecting transitions in a sleep state of the subject during the sleep session based on the output signals and baseline sleep state criteria, the baseline sleep state criteria comprising one or more thresholds for one or more corresponding parameters determined based on the information related to brain activity of the subject;

means for controlling the means for providing sensory stimuli to provide the sensory stimulation to the subject with a timing based on the detected transitions in the sleep state;

subsequent to the sleep session, means for obtaining reference indications of transitions in the sleep state, the reference indications of transitions in the sleep state being generated based on analysis of the output signals generated during the sleep session;

means for comparing the detected transitions in the sleep state to the reference indications of transitions in the sleep state, based on the comparison, means for adjusting the baseline sleep state criteria to enhance correlation between the detected transitions in the sleep state during the sleep session using the baseline sleep state criteria and the reference indications of transitions in the sleep state during the sleep session, and subsequent to adjustment of the baseline sleep state criteria, means for utilizing the adjusted baseline sleep state criteria to detect transitions in the sleep state of the subject and control the one or more sensory stimulators.

12. The system of claim 11, further comprising means for determining a performance metric related to slow wave activity in the subject that indicates whether the adjustment of the baseline sleep state criteria enhanced the correlation between the detected transitions in the sleep state during the sleep session using the baseline sleep state criteria and the reference indications of transitions in the sleep state during the sleep session.

13. The system of claim 12, wherein the means for determining a performance metric are configured such that the performance metric is cumulative slow wave activity.

14. The system of claim 13, wherein the means for adjusting are configured such that adjustment of the baseline sleep state criteria is based on an empirical estimation of a gradient of the cumulative slow wave activity.

15. A system configured to determine timing of sensory stimulation delivered to a subject during a sleep session, the sensory stimulation configured to increase slow wave activity and minimize arousals in the subject during the sleep session, the system comprising:

means for providing sensory stimuli to the subject;

means for generating output signals conveying information related to brain activity of the subject;

means for detecting transitions in a sleep state of the subject during the sleep session based on the output signals and baseline sleep state criteria;

means for controlling the means for providing sensory' stimuli to provide the sensory stimulation to the subject with a timing based on the detected transitions in the sleep state;

subsequent to the sleep session, means for obtaining reference indications of transitions in the sleep state, the reference indications of transitions in the sleep state being generated based on analysis of the output signals generated during the sleep session;

means for comparing the detected transitions in the sleep state to the reference indications of transitions in the sleep state;

based on the comparison, means for adjusting the baseline sleep state criteria to enhance correlation between the detected transitions in the sleep state during the sleep session using the baseline sleep state criteria and the reference indications of transitions in the sleep state during the sleep session;

subsequent to adjustment of the baseline sleep state criteria, means for utilizing the adjusted baseline sleep state criteria to detect, transitions in the sleep state of the subject and control the one or more sensory stimulators; and means for determining a performance metric related to slow wave activity that indicates whether the adjustment of the baseline sleep state criteria enhanced the correlation between the detected transitions in the sleep state during the sleep session using the baseline sleep state criteria and the reference indications of transitions in the sleep state during the sleep session, wherein the performance metric is cumulative slow wave activity, and wherein the cumulative slow wave activity is a summation of EEG power in a delta band for individual N2 and/or N3 sleep stage epochs for a pre-determined number of sleep cycles.

* * * * *